United States Patent [19]

Brange et al.

[11] Patent Number: 5,618,913
[45] Date of Patent: Apr. 8, 1997

[54] INSULIN ANALOGUES

[75] Inventors: Jens J. V. Brange, Klampenborg; Kjeld Norris, Hellerup; Mogens T. Hansen, Lynge, all of Denmark

[73] Assignee: Novo Nordisk A/S, Bagsvaerd, Denmark

[21] Appl. No.: 901,821

[22] Filed: Aug. 29, 1986

[30] Foreign Application Priority Data

Aug. 30, 1985 [DK] Denmark ................................ 3956/85
Oct. 14, 1985 [DK] Denmark ................................ 4677/85

[51] Int. Cl.$^6$ ............................ A61K 38/28; C07K 14/62
[52] U.S. Cl. ...................... 530/303; 435/69.4; 435/172.3; 930/DIG. 621
[58] Field of Search ............................... 530/303; 435/68, 435/172.3, 69, 70, 71, 68.1, 69.4; 514/3; 930/DIG. 621

[56] References Cited

U.S. PATENT DOCUMENTS

| | | | |
|---|---|---|---|
| 3,883,496 | 5/1975 | Geiger | 530/303 |
| 4,340,674 | 7/1982 | Manis et al. | 435/172.3 |
| 4,351,901 | 9/1982 | Bahl | 435/172.3 |
| 4,401,757 | 8/1983 | Morihara et al. | 435/71 |
| 4,411,994 | 10/1983 | Gilbert et al. | 435/172.3 |
| 4,565,785 | 1/1986 | Gilbert et al. | 435/172.3 |
| 4,645,740 | 2/1987 | Breddam et al. | 435/71 |
| 4,652,525 | 3/1987 | Rutter et al. | 435/172.3 |
| 5,008,241 | 4/1991 | Markussen et al. | 514/3 |
| 5,430,016 | 7/1995 | Balschmidt et al. | 514/4 |
| 5,559,094 | 9/1996 | Brems et al. | 514/3 |

FOREIGN PATENT DOCUMENTS 8300164 1/1983 WIPO .................................. 435/68

OTHER PUBLICATIONS

Keefer et al, Bioch. Biophys, Res. Comm., 100(3), 1229–36, (1981).
Bahl, U.S. S.I.R. H245, Apr. 7, 1987, (filed Jun. 29, 1981).
Marki et al, Hoppes—Seyler's Z. Physiol. Chem, 360, 1619–32, 1979 (Nov.).
Nature, 333, No. 6174, pp. 679–682, 10 Jun. 1988.
Brange et al, Diabetes, vol. 37, supp 1, May 1988.

*Primary Examiner*—David Saunders
*Attorney, Agent, or Firm*—Evenson, McKeown, Edwards & Lenahan, P.L.L.C.

[57] ABSTRACT

Novel rapid-acting human insulin analogues are provided having less tendency to self-association into dimers, tetramers, hexamers, or polymers. The novel human insulin analogues are formed by substituting one or more of the amino acid residues of human insulin with naturally occuring amino acid residues. The amino acid residue substitutions are preferably more hydrophilic than the natural amino acid residue at the respective position in the molecule. Furthermore, the insulin analogues have the same charge or a greater negative charge at neutral pH than that of human insulin. Preferred amino acid substitutions are Asp, Glu, Ser, Thr, His, and Ile, and more preferred substitutions are Asp and Glu. The novel insulin analogues can be used for the preparation of rapid-acting insulin solutions.

14 Claims, 5 Drawing Sheets

FIG. 1

```
    A         B         C         D         E
  35-mer    43-mer    32-mer    37-mer    36-mer 36-mer    42-mer    34-mer    37-mer    37-mer    33-mer
```

```
Lys Arg Phe Val Asn Gln His Leu Cys Gly Ser His Leu Tyr Ala Leu Glu Ala Leu Tyr Leu Val Cys
    Hinf I      Hpa I                           Nla IV              HindIII     Rsa I
AA AGA TTC GTT AAC CAA CAC TTG TGC GGT TCC CAC AGG GTG AAC CAA CTT CGA AAC ATG AAC CAA ACG-
   TCT AAG CAA TTG GTT GTG AAC ACG CCA AGG GTG TCC CAC TTG GTT GAA GCT TTG TAC TTG GTT TGC- Gly Glu Arg Gly Phe Phe Tyr Thr Pro Lys Ala Ala Lys Gly Ile Val Glu Gln Cys Cys Thr
  Hph I              MboII                   MstII,DdeI                     Taq I            Rsa I
GGT GAA AGA GGT TTC TTC TAC ACT CCT AAG GCT GCT AAG GGT ATT GTC GAA CAA TGC TGT ACC-
CCA CTT TCT CCA AAG AAG ATG TGA GGA TTC CGA CGA TTC CCA TAA CAG CTT GTT ACG ACA TGG- Ser Ile Cys Ser Leu Tyr Gln Leu Glu Asn Tyr Cys Asn
            Rsa I      (-PvuII)                            Hga I                    Xba I
TCC ATC TGC TCC TTG TAC CAA TTG GAA AAC TAC TGC AAC TAG ACG CAG CCC GCA GGC T
AGG TAG ACG AGG AAC ATG GTT AAC CTT TTG ATG ACG TTG ATC TGC GTC GGG CGT CCG AGA TC
```

FIG. 3
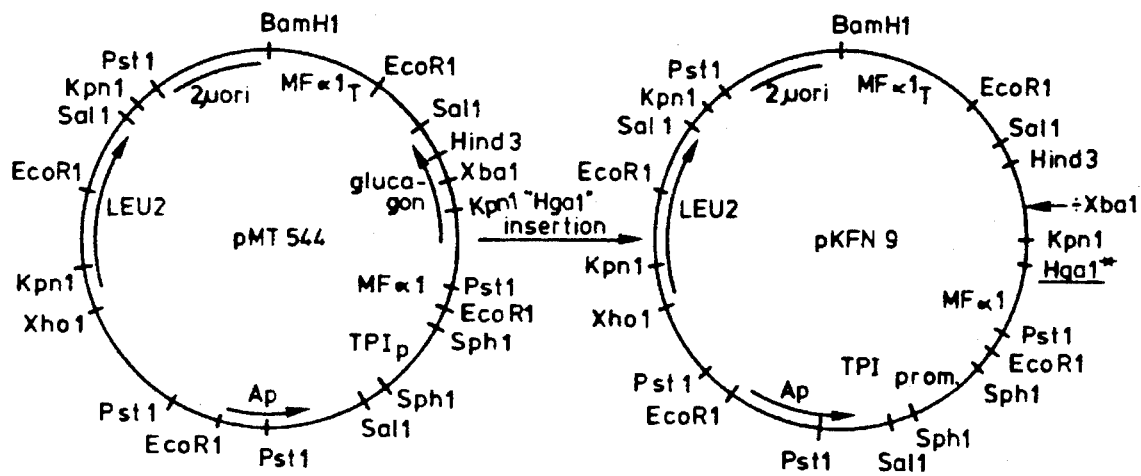
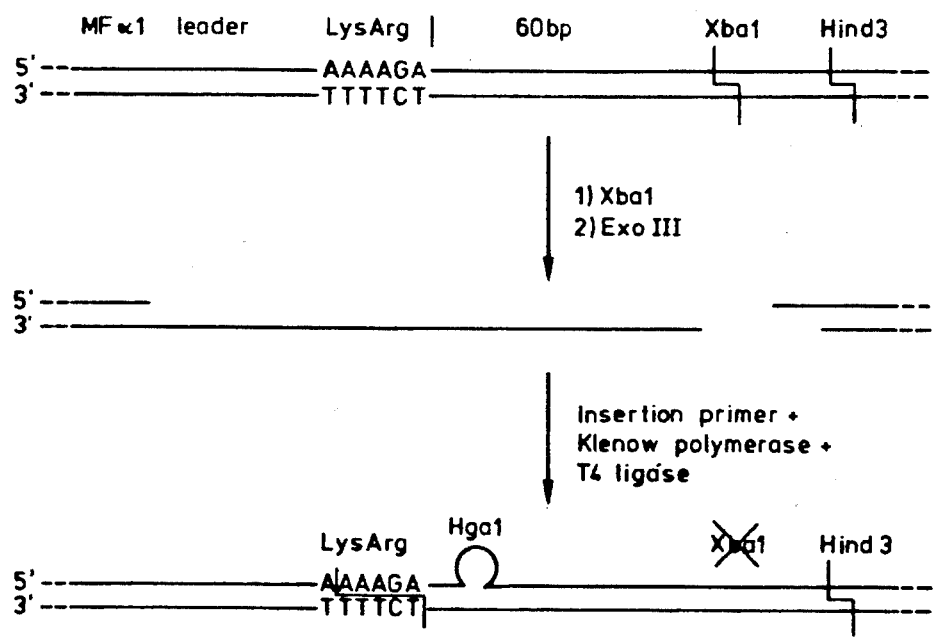

INSULIN ANALOGUES

The present invention relates to novel human insulin analogues characterized by a rapid onset of effect on subcutaneous injection and to injectable insulin solutions containing such insulin analogues and to methods for the preparation of the novel insulin analogues.

BACKGROUND OF THE INVENTION

In the treatment of Diabetes mellitus many varieties of insulin preparations have been suggested to the art. Some of these preparations are rapid-acting and others have a more or less prolonged action.

Rapid acting insulin preparations may be used in acute situations, such as hyperglycemic coma, during surgery, during pregnancy, and in severe infections. Furthermore, multiple, daily injections of rapid-acting insulin preparations may improve control in diabetics who have proved difficult to control with longer-acting insulin.

In the recent years there has been an increasing interest in an insulin treatment which approaches the insulin secretion from the beta-cells of the healthy organism, i.e. supply of insulin in connection with meals and maintenance of a basal insulin level. Clinical investigations have shown that diabetics can obtain nearly normal insulin and glucose concentrations by means of one daily injection of insulin with prolonged action to cover the basal need, supplemented with injections of smaller amounts (bolus) of rapid-acting insulin before the main meals.

Rapid-acting insulins are also used in mixtures with intermediate and long-acting insulins for treatment of diabetics requiring a stronger initial effect in addition to the delayed action of intermediate and long-acting insulins.

Finally, rapid-acting insulin is used in continuous insulin delivery systems.

By subcutaneous injection of rapid-acting insulin solutions an initial delay in absorption has been observed (Binder, Diabetes Care 7, No. 2 (1984), 188–199). A delay in absorption resulting in a slower onset of action is however undesirable when a strict metabolic control is aimed at. Mixing of rapid-acting insulin solutions with longer-acting insulin preparations may furthermore result in reduced rate of absorption of the rapid-acting insulin.

Accordingly, there is a need for rapid-acting insulin solutions with a faster onset of action upon subcutaneous injection and an improved miscibility with protracted insulin preparations.

A further drawback of known rapid-acting insulin solution is the tendency of insulin to fibrillate and precipitate out in the insulin solutions used for continuous insulin delivery thereby obstructing mechanical parts and delivery catheters.

Finally there is a need for alternative insulin preparations for the treatment of patients resistent to normal insulin.

It is the object of the present invention to provide novel rapid-acting insulin solutions with one or more of the following improved properties:

1) faster onset of action by subcutaneous injection or other routes of administration
2) improved miscibility with protracted insulin preparations
3) reduced tendency to fibrillation when used in implantable delivery systems, and
4) usable for the treatment of resistent patients (low affinity for preexisting antibodies).

The objectives of this invention are achieved with injectable aqueous solutions of the novel human insulin analogues hereinafter described.

A large number of insulin analogues have been described in the past. Märki et al. (Hoppe-Seyler's Z. Physiol.Chem., 360 (1979), 1619–1632) describe synthesis of analogues of human insulin that differ from human insulin in the replacement of a single amino acid in positions 2, 5, 6, 7, 8, and 11 of the A-chain and 5, 7, 13, and 16 of the B-chain affording new insights into the intriguing structure-activity relationship of insulin. Further studies modified the major receptor binding area in insulin (B(22)–B(26)) to investigate the impact of such mutation on the receptor binding activity. The known human insulin analogues will, however, not exhibit the properties desired by the inventors hereof.

It is known that sulphated insulins have a substantially lower tendency to fibrillation (Albisser et al., Desired Characteristics of insulin to be used in infusion pumps. In: Gueriguian J.L. et al., eds. US Pharmacopeial Convention, Rockwille, Md., pp. 84–95) and exhibit a low antigenicity. Sulphated insulins are, however, a heterogeneous mixture of at least nine different insulin derivatives containing on average 4.5 sulphate ester groups per molecule. Sulphated insulins have furthermore a reduced insulin activity, being about 20% of the activity of native insulin. A further drawback of sulphated insulins as compared to native insulin is that they needlessly contain amino acid residues which are chemically modified, i.e. amino acids which do not occur naturally.

It is therefore a further object of the present invention to provide insulin analogues which are homogeneous, have a higher biological activity than sulphated insulins and which furthermore preferably only contain naturally occuring amino acids.

By "insulin analogues" as used herein is meant a compound having a molecular structure similar to that of human insulin including the disulphide bridges between A(7)Cys and B(7)Cys and between A(20)Cys and B(19)Cys and an internal disulphide bridge between A(6)Cys and A(11)Cys and with insulin activity.

SUMMARY OF THE INVENTION

The present invention is based on the surprising fact that certain insulin analogues, in which at least one of the amino acid residues of human insulin has been substituted with naturally occuring amino acid residues, exhibit the desired rapid acting activity.

In its broadest aspect the present invention provides novel, rapid-acting human insulin analogues formed by substituting one or more of the amino acid residues of human insulin with naturally occuring amino acid residues giving rise to less self-association into dimers, tetramers, hexamers, or polymers, and having the same charge or a greater negative charge at neutral pH than that of human insulin.

To provide a reduced tendency to self-association into dimers, tetramers, hexamers, or polymers certain residues of human insulin are preferably substituted with other amino acid residues being more hydrophilic than the natural amino acid residue at the respective position in the molecule. Also, at certain positions in the insulin molecule substitution with a more bulky amino acid residue will give rise to a reduced tendency of the insulin molecules to associate into dimers, tetramers, hexamers, or polymers.

More specifically the present invention provides novel insulin derivatives with the following general formula (I):

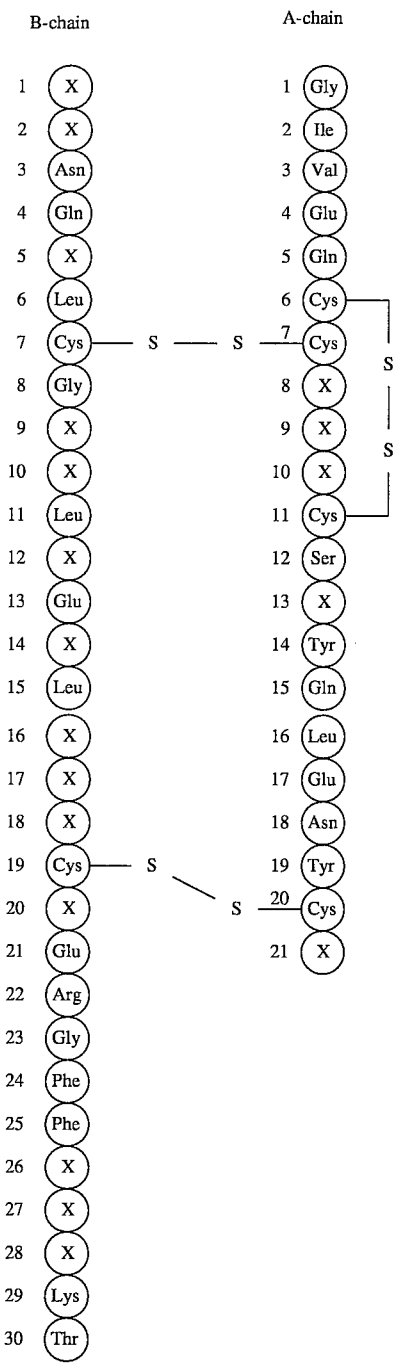

wherein the X's are the amino acid residues of human insulin or the same of different amino acid residue substitutions, the net function of which are to impart to the molecule the same charge or a greater negative charge at neutral pH than that of human insulin, with the proviso that at least one X is different from the amino acid residues of human insulin at the respective position in the insulin molecule and that when X in position A(8) is His or Phe, X in position A(21) is Asp, X in position B(5) is Ala, X in position B(9) is Leu, X in position B(10) is Asn or Leu, X in position B(12) is Asn or X in position B(26) is Ala, then at least one of the remaining X's are different from the amino acid residues of human insulin at the respective position in the insulin molecule, and with the further proviso that one or more amino acid residues may have been removed from the N- and/or C-terminal ends of the A- and/or B-chain.

Preferably at least a majority of the amino acid residue substitutions are more hydrophilic than the amino acid residue at the corresponding site in the human insulin molecule and more preferably all amino acid residue substitutions are more hydrophilic than the corresponding human insulin amino acid residues.

With respect to hydrophilicity reference is made to C. Frömmel, J. Theor. Biol. 111 (1984), 247–260 (table 1).

With reference to the above formula I preferably not more than about 7 of the X's are different from the amino acid residue at the corresponding position in the human insulin molecule. More preferred are 2–4 substitutions.

BRIEF DESCRIPTION OF THE DRAWINGS

FIG. 1 shows a synthetic gene encoding B(1–29)-Ala-Ala-Lys-A(1–21)human insulin.

FIG. 3 shows the construction of plasmid pKFN9.

PREFERRED EMBODIMENTS OF THE INVENTION

Figure 2:
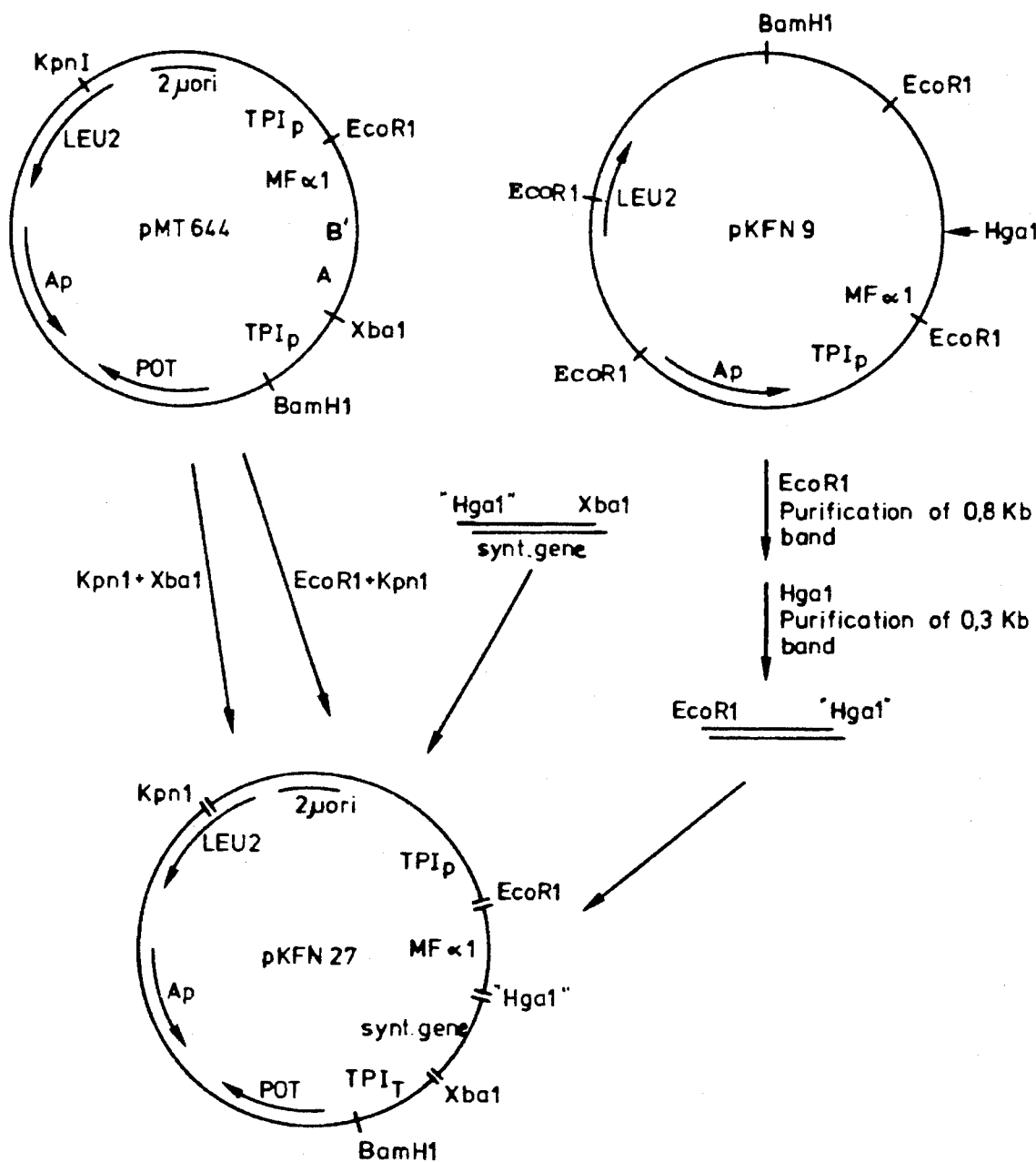
FIG. 2 shows the contruction of plasmid pKFN27.

The amino acid residues substitutions are preferably chosen among the group consisting of Asp, Glu, Ser, Thr, His, and Ile and are more preferably negatively charged amino acid residues, i.e. Asp and/or Glu.

The novel human insulin analogue may preferably contain Asp and/or Glu instead of one or more of the hydroxy amino acids of human insulin, or instead of one or more Gln and Asn of human insulin.

The novel human insulin analogues may furthermore preferably contain Ser and/or Thr or Asp and/or Glu instead of one or more of the amino acid residues of human insulin with an aliphatic and/or aromatic side chain.

The novel human insulin analogues may also preferably contain His instead of one or more of the amino acid residues of human insulin with an aliphatic and/or aromatic side chain or instead of one or more of the hydroxy amino acids of human insulin.

Preferred sites of substitutions are at the sites B9, B10, B12, B26, B27, and B28, preferably B9, B12, B27, and B28, in which positions one substitution can be sufficient for obtaining a reduced tendency to self-association and a more rapid-action by administration.

The amino acid residue substitution in position B9 may be chosen from the group consisting of Asp, Pro, Glu, Ile, Leu, Val, His, Thr, Gln, Asn, Met, Tyr, Trp and Phe and more preferably from the group consisting of Asp, Glu, Gln, Asn, and His.

The amino acid residue substitution in position B12 may be chosen from the group consisting of Ile and Tyr. The amino acid residue substitution in position B10 may be chosen from the group consisting of Asp, Arg, Glu, Asn, and Gln and in positions B26, B27, and B28 the amino acid residue substitutions are preferably Asp or Glu.

In the remaining positions of the insulin molecule at least two substitutions (preferably in combination with the above mentioned positions) seem to be necessary to obtain the improved properties. In these positions substitutions may be made as follows:

| Position | Preferred amino acid residue substitutions |
| --- | --- |
| A8 | His, Gly, Gln, Glu, Ser, Asn, Asp, Pro |
| A9 | Gly, Asp, Glu, Thr, His, Gln, Asn, Ala, Pro |
| A10 | Leu, Pro, Val, His, Ala, Glu, Asp, Thr, Gln, Asn |
| A13 | Pro, Val, Arg, His, Ala, Glu, Asp, Thr, Gly, Gln, Asn, Asp |
| A21 | Asp, Glu |
| B1 | Glu, Asp, Thr, Ser |
| B2 | Arg, His, Ala, Glu, Asp, Thr, Pro, Gly, Gln, Ser, Asn |
| B5 | Glu, Asp, Thr, Ser, Gln, Asn |
| B14 | Glu, Asp, Asn, Gln, Ser, Thr, Gly |
| B16 | Asp, Glu, Gln, Asn, Ser, Thr, His, Arg |
| B17 | Ser, Thr, Asn, Gln, Glu, Asp, His |
| B18 | Ser, Thr, Asn, Gln, His |
| B20 | Gln, Ser, Asn, Asp, Glu, Arg |

Further preferred compounds of the present invention are insulin analogues in which substitutions are at the following sites: B27, B12, B9, (B27+B9), (B27+A21), (B27+B12), (B12+A21), (B27+B17), (B27+A13), (B27+B16), (B27+A10), (B27+B28), (B27+B26), (B27+B10), (B27+B1), (B27+B2), (B27+B5), (B27+B14), (B27+B18), (B27+B20), (B12+B17), (B12+A10), (B12+A13), (B12+B16), (B12+B1), (B12+B2), (B12+B5), (B12+B10), (B12+B26), (B12+B28), (B9+B17), (B9+A13), (B9+B16), (B9+A8), (B9+A9), (B9+A10), (B9+B1), (B9+B2), (B9+B5), (B9+B10), (B9+B12), (B9+B14), (B9+B28), (B9+B18), (B9+B20), (B9+B26), (B27+B9+A21), (B9+B27+A8) (B27+B12+A21), (B27+B12+B9), (B9+B12+B27+B17), (B9+B12+B27+A13), (B9+B12+B27+B16) and (B12+B16+B17+B27+A10+A13).

Preferred embodiments of the above formula I are as follows:

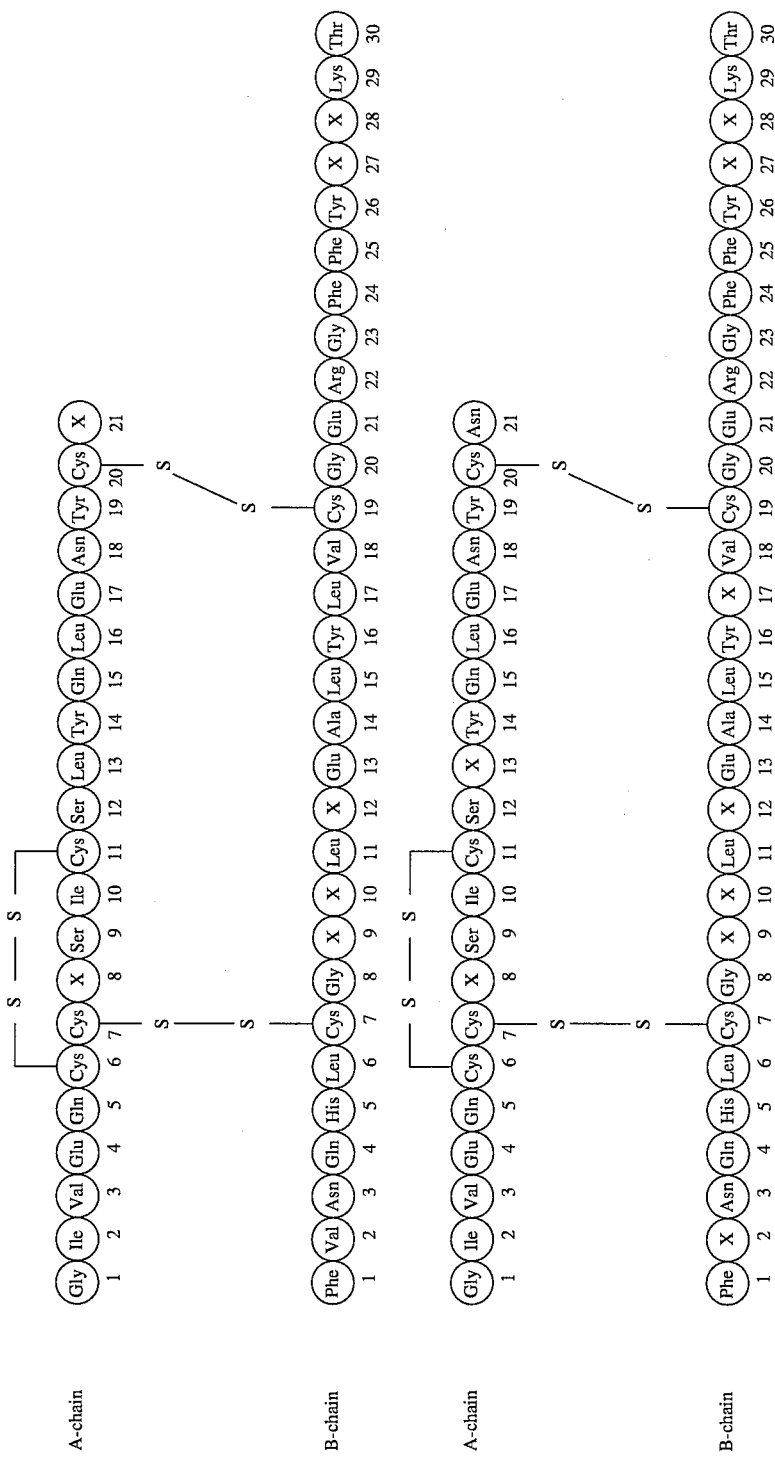

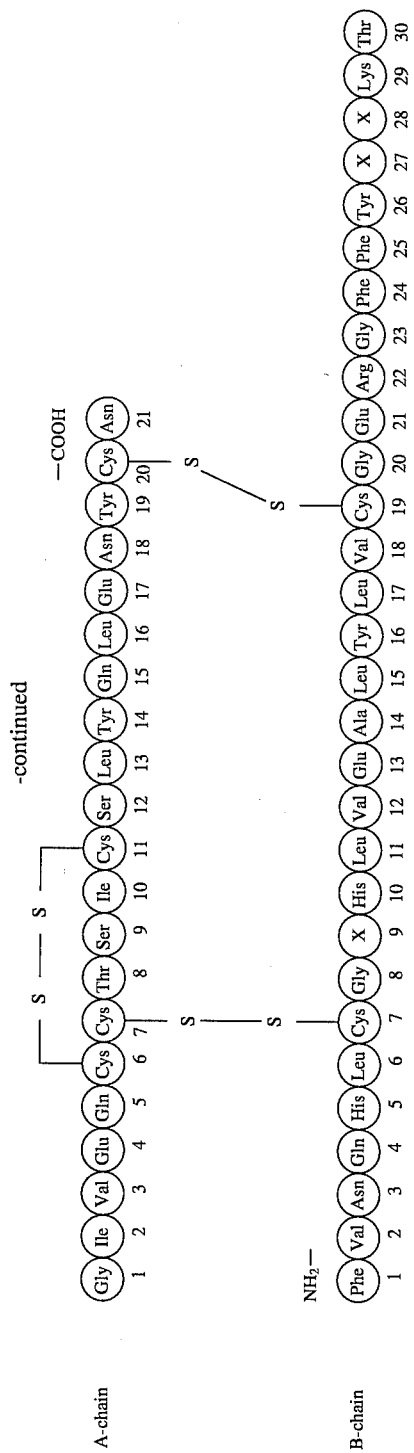

in which the X's are defined as above.

Referring to formula I other preferred insulin analogues according to the present invention are such in which X in position B27 is Glu, X in position B12 is Ile or Tyr, X in position A21 is Asp and in position B27 is Glu, X in position B9 is Asp, X in position A21 and in position B9 is Asp and in position B27 is Glu, X in position A8 is His, in position B9 is Asp and in position B27 is Glu, X in position B10 is Asp, X in position B28 is Asp, or X in position B9 is Asp and in position B27 is Glu.

According to a second aspect of the present invention there are provided injectable solutions with insulin activity. The injectable insulin solutions of this invention contain the human insulin analogues described above or a pharmaceutically acceptable salt thereof in aqueous solution preferably at neutral pH. The aqueous medium may be made isotonic by addition of for example sodium chloride and glycerol. Also buffers, such as an acetate or citrate and preservatives, such as m-cresol, phenol or methyl 4-hydroxy benzoate may be added. The insulin solutions may furthermore contain zinc ions.

The human insulin analogues of this invention may be substituted for human or porcine insulin in the rapid acting insulin solutions heretofore known to the art.

PREPARATION OF THE INSULIN ANALOGUES

After the advent of the recombinant DNA-technology the possibilities for the protein engineering has become to be enormous. By the socalled site specific mutagenesis technique it is possible to alter a gene coding for a naturally occurring protein by substituting any one or more of the codons in the native gene with codon(s) for other naturally occuring amino acid(s). Alternatively the modified gene may be made by chemical synthetesis of the total DNA-sequence by well known technique. The purpose of such manipulation of a gene for a natural protein will typically be to alter the properties of the natural protein in one or another aimed direction.

The novel insulin analogues may be prepared by altering the proinsulin gene through replacement of codon(s) at the appropriate site in the native human proinsulin gene by codon(s) encoding the desired amino acid residue substitute(s) or by synthesizing the whole DNA-sequence encoding the desired human insulin analogue. The novel modified or synthetic gene encoding the desired insulin analogue is then inserted into a suitable expression vector which when transferred to a suitable host organism, e.g. *E. coli*, Bacillus or a yeast, generates the desired product. The expressed product is then isolated from the cells or the culture broth depending on whether the expressed product is secreted from the cells or not.

The novel insulin analogues may also be prepared by chemical synthesis by methods analogue to the method described by Märki et al. (Hoppe-Seyler's Z. Physiol. Chem., 360 (1979), 1619–1632). They may also be formed from separately in vitro prepared A- and B-chains containing the appropriate amino acid residue substitutions, whereupon the modified A- and B-chains are linked together by establishing disulphide bridges according to known methods (e.g. Chance et al., In: Rick DH, Gross E (eds) Peptides: Synthesis - Structure - Function. Proceedings of the seventh American peptid symposium, Illinois, pp 721–728).

The novel insulin analogues are preferably prepared by reacting a biosynthetic precursor of the general formula II:

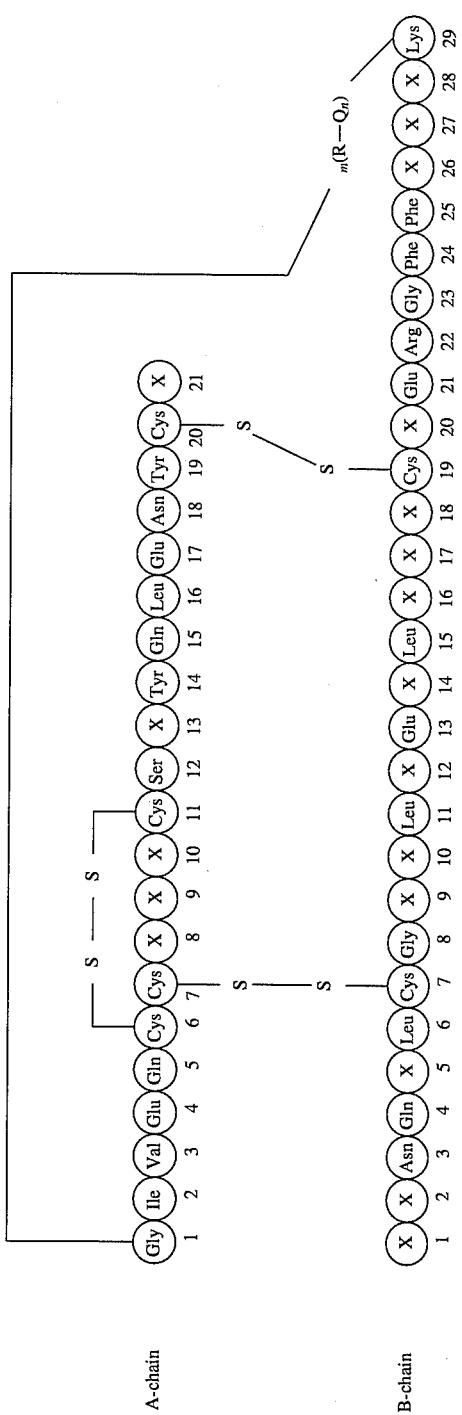

wherein $Q_n$ is a peptide chain with n naturally occuring amino acid residues, R is Lys or Arg, n is an integer from 0 to 33, m is 0 or 1, and the X's are defined as above with the proviso that the peptide chain —$Q_n$—R— does not contain two adjacent basic amino acid residues, with an L-threonine ester in the presence of trypsin or a trypsin derivative followed by conversion of the obtained threonine ester of the human insulin analogue into the human insulin analogue by known methods. This socalled "transpeptidation" reaction is described in U.S. Pat. No. 4,343,898 (the disclosures of which are incorporated by reference hereinto).

By the transpeptidation reaction the bridging —($Q_n$—R)$_m$— between amino acid 29 in the B chain and amino acid 1 in the A chain is excised and a threonine ester group is coupled to the C terminal end of B29Lys.

The precursors of the above formula II may be prepared by a method analogue to the method described in EP patent application No. 0163529A the disclosure of which is incorporated by reference hereinto. By this method a DNA-sequence encoding the precursor in question is inserted in a suitable expression vehicle which when transferred to yeast is capable of expressing and secreting the desired compound with correctly positioned disulphide bridges. The expressed product is then isolated from the culture broth.

The present insulin analogues may also be prepared by reacting a biosynthetic precursor of the general formula III:

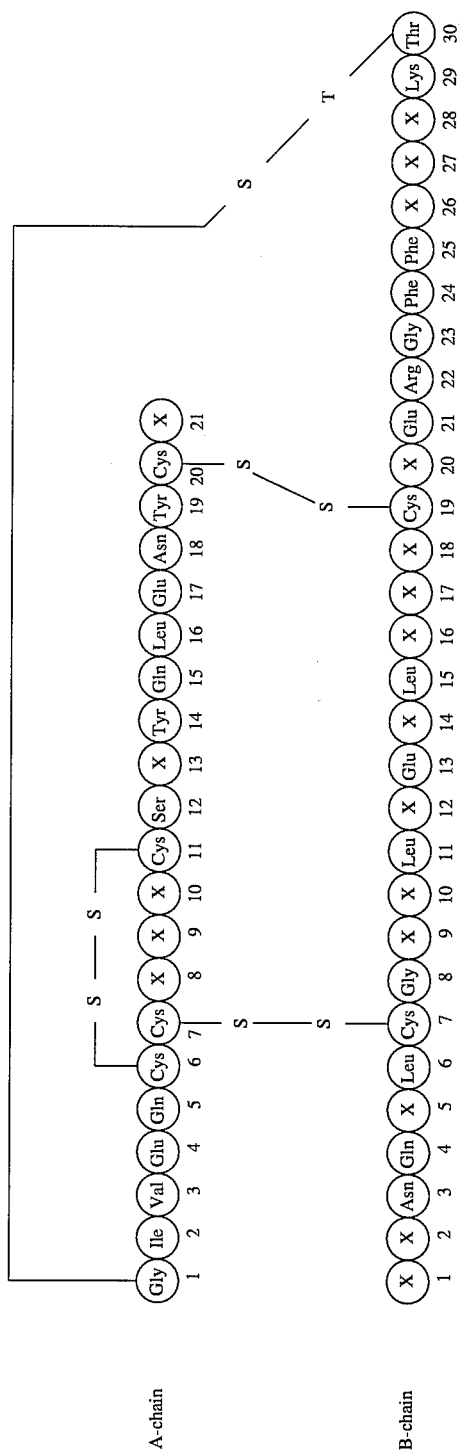

wherein S and T are each Lys or Arg and the X's are defined as above, in aqueous solution with trypsin and carboxypeptidase B and recovering the human insulin analogue from the reaction solution.

The precursors of the above formula III may be prepared by a method analogue to the method described in EP patent application No. 86302133.3 the disclosure of which is incorporated by reference hereinto. By this method a DNA-sequence encoding the precursor is inserted into a suitable yeast expression vehicle which, when transferred to yeast is capable of expression and secretion of the expressed product with correctly positioned disulphide bridges into the culture medium.

According to a third aspect of the present invention there is provided a method for producing of the novel insulin analogues by which method a yeast strain containing a replicable expression vehicle comprising a DNA-sequence encoding a precursor of the insulin analogue is cultured in a suitable nutrient medium, and the precursor is recovered from the culture medium and converted into the novel insulin analogue by enzymatic and chemical in vitro conversion.

The present invention is also directed to novel precursors of the novel insulin analogues, DNA sequences encoding such novel precursors, expression vehicles containing such DNA-sequences and yeast strains transformed with such expression vehicles.

MODIFIED INSULIN ANALOGUES

The present invention is contemplated to comprise certain derivations or further substitutions of the insulin analogues provided that such derivations or further substitutions have no substantial impact on the above-described goal of the invention. It is accordingly possible to derivate one or more of the functional groups in the amino acid residues. Examples of such derivation is per se known conversion of acid groups in the insulin molecule into ester or amid groups, conversion of alcohol groups into alkoxy groups or vice versa, and selective deamidation. As an example A21Asn may be deamidated into A21Asp by hydrolysis in acid medium or B3Asn may be deamidated into B3Asp in neutral medium.

It is furthermore possible to modify the present insulin analogues by either adding or removing amino acid residues at the N- or C-terminal ends. The insulin analogues of the present invention may lack up to four amino acid residues at the N-terminal end of the B-chain and up to five amino acid residues at the C-terminal end of the B-chain without significant impact on the overall properties of the insulin analogue. Examples of such modified insulin analogues are insulin analogue lacking the B1Phe or the B30Thr amino acid residue.

Also, naturally occurring amino acid residues may be added at one or more ends of the polypeptide chains provided that this has no significant influence on the above-described goal.

Such deletions or additions at the ends of the polypeptide chain of the present insulin analogues may be exercised in vitro on the insulin analogues with amino acid substitutions according to the present invention. Alternatively the gene for the novel insulin analogues according to the present invention may be modified by either adding or removing codons corresponding to the extra amino acid residues or lacking amino acid residues at the ends of the polypeptide chain, respectively.

TERMINOLOGY

The abreviations used for the amino acids are those stated in J.Biol.Chem. 243 (1968), 3558. The amino acids are in the L configuration.

As used in the following text B(1–29) means a shortened B chain of human insulin from B1Phe to B29Lys and A(1–21) means the A chain of human insulin.

The substitution(s) made in the human insulin molecule according to the practice of the invention is(are) indicated with a prefix referenced to human insulin. As an example B27Glu human insulin means a human insulin analogue wherein Glu has been substituted for Thr in position 27 in the B chain. B27Glu,B9Asp human insulin means a human insulin analogue wherein Glu has been substituted for Thr in position 27 in the B chain and Asp has been substituted for Ser in position 9 in the B chain. B27Glu,B(1–29)-Ala-Ala-Lys-A(1–21) human insulin means a precursor for the insulin analogue (see formula II) wherein Glu has been substituted for Thr in position 27 in the shortened B chain (see above) and wherein the B(1–29)-chain and the A-chain (A(1–21)) are connected by the peptide sequence Ala-Ala-Lys. Unless otherwise stated it is to be understood that the B(1–29) chain and A(1–21) chain are connected by disulphide bridges between A(7)Cys and B(7)Cys and between A(20)Cys and B(19)Cys, respectively, as in human insulin and that the A chain contains the internal disulphide bridge between A (6) Cys and A(11)Cys.

EXPLANATION OF THE INVENTION

As has already been pointed out, the objective of this invention is to provide rapid acting injectable insulin solutions. In effort to meet this objective, the inventors hereof recognized first and foremost that considerable differences exist between insulin in a depot or bolus and insulin in the circulation, including notably a completely unavoidable difference in insulin concentration. Specifically, insulin in the bloodstream is highly dilute, being $10^{-11}$ to $10^{-8}$M and is in monomer form, with possibly some insulin being in dimer form. The much more concentrated insulin stored in the B-cell granule of pancreas and in the usual administerable solution is largely, if not principally, in the non-active hexamer form, for example, as the well-known 2 zinc hexamer.

Human insulin in solution is known to exist in many molecular forms, namely, the monomer, the dimer, the tetramer and the hexamer (Blundell et al. in Advances in Protein Chemistry, Academic Press, New York and London, Vol. 26, pp. 279–330, 1972), with the oligomer forms being favored at high insulin concentrations and the monomer beina the active form of insulin. The tetramer and hexamer are not active forms, and even the dimer may not be active. The concept underlying this invention is the inventor's belief that the art recognized delayed absorption phenomena (Binder, Diabetes Care 7, No. 2 (1984), 188–199) is in some large part attributable to the time required for the insulin to disassociate from hexamer, tetramer and dimer form into the (active) monomer form.

The human insulin analogues of this invention achieve their rapid action through a molecular structure not readily susceptible of dimer, tetramer, hexamer, or polymer formation, i.e. with a reduced tendency to self-associate into dimers, tetramers, hexamers, or polymers Kith or without the presence of zinc ions.

It has long been recognized from the considerable species-to-species differences in amino acid sequence which exist in insulin that not all of the amino acid residues present in the insulin molecule are crucial to insulin activity, and that some of the amino acids not essential to insulin activity are important to the physical properties of the insulin molecule. Indeed, guinea pig insulin is known to be incapable of dimerizing. Sulfated insulin and tetranitro tyrosine insulin do not dimerize. Thus, many of the amino acid residues in the Pluman insulin molecule may be changed without substantial decrease in insulin activity. The amino acid substitutions in the human insulin molecule herein contemplated are directed to preventing formation of dimers, tetramers, hexamers, or polymers without destroying the insulin activity.

The amino acid residues in the positions in the A chain and the B chain of Formula I where substitutions may be made are not crucial to the insulin activity, but they are important to the capability of human insulin to aggregate into dimers, tetramers, hexamers, or polymers, or for the solubility of the human insulin. The present amino acid residue substitutions interfere with the atom-to-atom contacts between adjacent insulin molecules that facilitates aggregation into dimers, tetramers, hexamers or polymers.

As might be expected for substitution purposes, changes in certain positions in the human insulin molecule are more effective than others. By and large, a single substitution made in the B-chain may be sufficient to lessen the self-associating tendency, whereas at least two changes of other residues may be required. The substitutions in the A-chain mainly serve to improve the solubility of the dissociated molecule. Preferred positions for making amino acid residue substitutions are B9, B12, B10, B26, B27, and B28 alone, in combination with each other or together with substitutions elsewhere in the insulin molecule as indicated in formula I.

Manifestly, substitution of one or more negatively charged amino acid residues for an uncharged or positively charged amino acid residue is to make the charge of the human insulin analogue more negative at neutral pH and lower the isoelectric point visa vis human insulin. Characteristically, the human insulin analogues of this invention have the same or a more negative charge (at neutral pH) and a lower isoelectric point than human insulin.

By and large, from 1 to 3 substitutions will achieve the immediate objectives of this invention, namely, provide a more rapid action insulin, and such do constitute preferred modes of the invention. By using 2–3 substitutions an improved miscibility with protected insulin preparations may be achieved. However, it is believed advantageous that the immediate objectives of this invention can be achieved, also, through a greater number of substitutions than three, since desirable secondary objectives may be achieved thereby.

In particular, an additional level of substitution, say presence of 4 or 5 substitute amino acid residues, may result in a human insulin analogue that also is less subject to fibrillation, or interface polymerization, a characteristic particularly desirable when the insulin solution is intended for continuous infusion. By and large, not more than about 7 substitutions in the insulin molecule are contemplated for the human insulin analogue of this invention. Preferred are 2–4 substitutions.

DETAILED DESCRIPTION

Genes encoding the precursors of the present insulin analogues can be prepared by modification of genes encoding the above insulin precursors with formula (II) (or III) in which all X's are the amino acid residues of human insulin by site specific mutagenesis to insert or substitute with codons encoding the desired mutation. A DNA-sequence encoding the precursor of the insulin analogue may also be made by enzymatic synthesis from oligonucleotides corresponding in whole or part to the insulin analogue precursor gene.

DNA-sequences containing a gene with the desired mutation of the insulin gene are then combined with fragments coding for the TPI promoter (TPIp) (T. Alber and G. Kawasaki. Nucleotide Sequence of the Triose Phosphate Isomerase Gene of Saccharomyces cerevisiae. J. Mol.Applied Genet. 1 (1982) 419–434), the MFα1 leader sequence (J. Kurjan and I. Herskowitz,. Structure of a Yeast Pheromone Gene (MFα1): A Putative α-Factor Precursor Contains four Tandem Copies of Mature α-Factor. Cell 30 (1982) 933–943) and the transcription termination sequence from TPI of S. cerevisiae ($TPI_T$). These fragments provide sequences to ensure a high rate of transcription for precursor encoding gene and also provide a presequence which can effect the localization of precursor into the secretory pathway and its eventual excretion into the growth medium. The expression units are furthermore provided with the yeast 2μ origin of replication and a selectable marker, LEU 2.

During in vivo maturation of α-factor in yeast, the last (C-terminal) six amino acids of the MFα1 leader peptide (Lys-Arg-Glu-Ala-Glu-Ala) are removed from the α-factor precursor by the sequential action of an endopeptidase recognizing the Lys-Arg sequence and an aminodipeptidase which removes the Glu-Ala residues (Julius, D. et al. Cell 32 (1983) 839–852). To eliminate the need for the yeast aminodipeptidase, the sequence coding for the C-terminal Glu-Ala-Glu-Ala of the MFα1 leader was removed from the MFα1 leader sequence by in vitro mutagenesis. In the following text "MFα1 leader" means the whole leader sequence whereas MFα1 leader (minus Glu-Ala-Glu-Ala) means a leader sequence wherein the C-terminal Glu-Ala-Glu-Ala sequence has been removed.

EXAMPLE 1

Construction of a Synthetic Gene Encoding B(1–29)-Ala-Ala-Lys-A(1–21) Human Insulin A yeast codon optimized structural gene for B(1–29)-Ala-Ala-Lys-A(1–21) human insulin was constructed as follows.

The following 10 oligonucleotides were synthesized on an automatic DNA synthesizer using phosphoramidite chemistry on a controlled pore glass support (S.L. Beaucage and M.H. Caruthers (1981) Tetrahydron Letters 22, 1859–1869):

| | |
|---|---|
| I: | AAAGATTCGTTAACCAACACTTGTGCGGTTCCCAC |
| | 35-mer |
| II: | AACCAAGTGGGAACCGCACAAGTGTTGGTTAACGAA |
| | 36-mer |
| III: | TTGGTTGAAGCTTTGTACTTGGTTTGCGGTGAAAGAGGTTTCT |
| | 43-mer |

| | |
|---|---|
| IV: | GTAGAAGAAACCTCTTTCACCGCAAACCAAGTACAAAGCTTC |
| | 42-mer |
| V: | TCTACACTCCTAAGGCTGCTAAGGGTATTGTC |
| | 32-mer |
| VI: | ATTGTTCGACAATACCCTTAGCAGCCTTACCAGT |
| | 34-mer |
| VII: | GAACAATGCTGTACCTCCATCTGCTCCTTGTACCAAT |
| | 37-mer |
| VIII: | TTTTCCAATTGGTACAAGGAGCAGATGGAGGTACAGC |
| | 37-mer |
| IX: | TGGAAAACTACTGCAACTAGACGCAGCCCGCAGGCT |
| | 36-mer |
| X: | CTAGAGCCTGCGGGCTGCGTCTAGTTGCAGTAG |
| | 33-mer |

5 duplexes A–E were formed from the above 10 oligonucleotides as indicated on FIG. 1.

20 pmole of each of the duplexes A–E was formed from the corresponding pairs of 5'-phosphorylated oligonucleotides I–X by heating for 5 min. at 90° C. followed by cooling to room temperature over a period of 75 min. The 33-mer (X) in duplex E was not 5'-phosphorylated in order to avoid dimerization around the self complementary XbaI single stranded ends fluring the ligation. The five duplexes were mixed and treated with T4 ligase. The synthetic gene was isolated as a 182/183 bp band after electrophoresis of the ligation mixture on a 2% agarose gel.

The obtained synthetic gene is shown in FIG. 1.

The synthetic gene was ligated to a 4 kb Kpn1-EcoR1 fragment and a 8 kb Xba1-Kpn1 fragment from pMT644 and a 0.3 kb EcoR1-HgaI fragment from pKFN9 to give the following structure $TpI_p$-MFα1 leader-B(1–29)-Ala-Ala-LYs-A(1–21)-$TPI_T$.

Plasmid pMT644 contains the DNA-sequence $TpI_p$-MFα1 leader-B(1–29)-A(1–21)-$TpI_T$ and the construction is described in Danish patent specification No. 1293/85. The construction of plasmid pKFN9 is described in the following.

The ligation mixture was used to transform competent *E. coli* strain (r⁻,m⁺) (MT172). 30 ampicillin resistent colonies were transferred to plates containing minimal medium M9 (T. Maniatis et al., Molecular Cloning, Cold Spring Harbor Laboratory, 1982, p. 68) resulting in 8 Leu⁺ colonies. Maxam-Gilbert sequencing of a $^{32}$P-Xba1-EcoR1 fragment showed that three plasmids contained a gene with the desired sequence. One plasmid pKFN27 was selected for further use.

The construction of pKFN27 is illustrated in FIG. 2.

Construction of Plasmid pKFN9

The purpose of construction of plasmid pKFN9 was to obtain a plasmid containing a Hga1 site immediately after the MFα1-leader sequence. Plasmid pMT544 (the construction of which is described in Danish patent specification No. 278/85) was cut with Xba1 and about 250 bases were removed from the 3'ends with ExoIII nuclease treatment. A synthetic 32-mer insertion primer GGATAAAGAGAG-GCGCGTCTGAAGCTCACTC containing a Hga1 sequence was annealed to the partly single stranded DNA. A double stranded circular DNA was made by filling in with Klenow polymerase and ligation with T4 ligase. After transformation of *E. coli* (r⁻,m⁺) (MT 172) colonies containing mutated plasmid were identified by colony hybridization with 5'-$^{32}$P-labelled 32-mer insertion primer. The occurence of a new Hqa1 site was confirmed with restriction enzyme cutting (EcoR1+Hga1, Hind3+Hga1). After retransformation a "pure" mutant pKFN9 was selected for further use. The construction of pKFN9 is illustrated in FIG. 3.

EXAMPLE 2

Preparation of B27Glu Human Insulin

B27Glu human insulin was prepared by transpeptidation of B27Glu,B(1–29)-Ala-Ala-Lys-A(1–21) human insulin with Thr-OBu$^t$ and acidolysis of the obtained threonine ester with trifluoracetic acid. The preparation consisted of the following steps:

I. Construction of a Gene Encoding B27Glu, B(1–29)-Ala-Ala-Lys-A(1–21) Insulin Plasmid pKFN27 was linearized in the unique Xba1 site just downstream of the synthetic insulin precursor gene. In order not to destroy the Xba1 site by the filling in step described below a 19-mer Hind3-Xba1 double stranded linker

Figure 4:
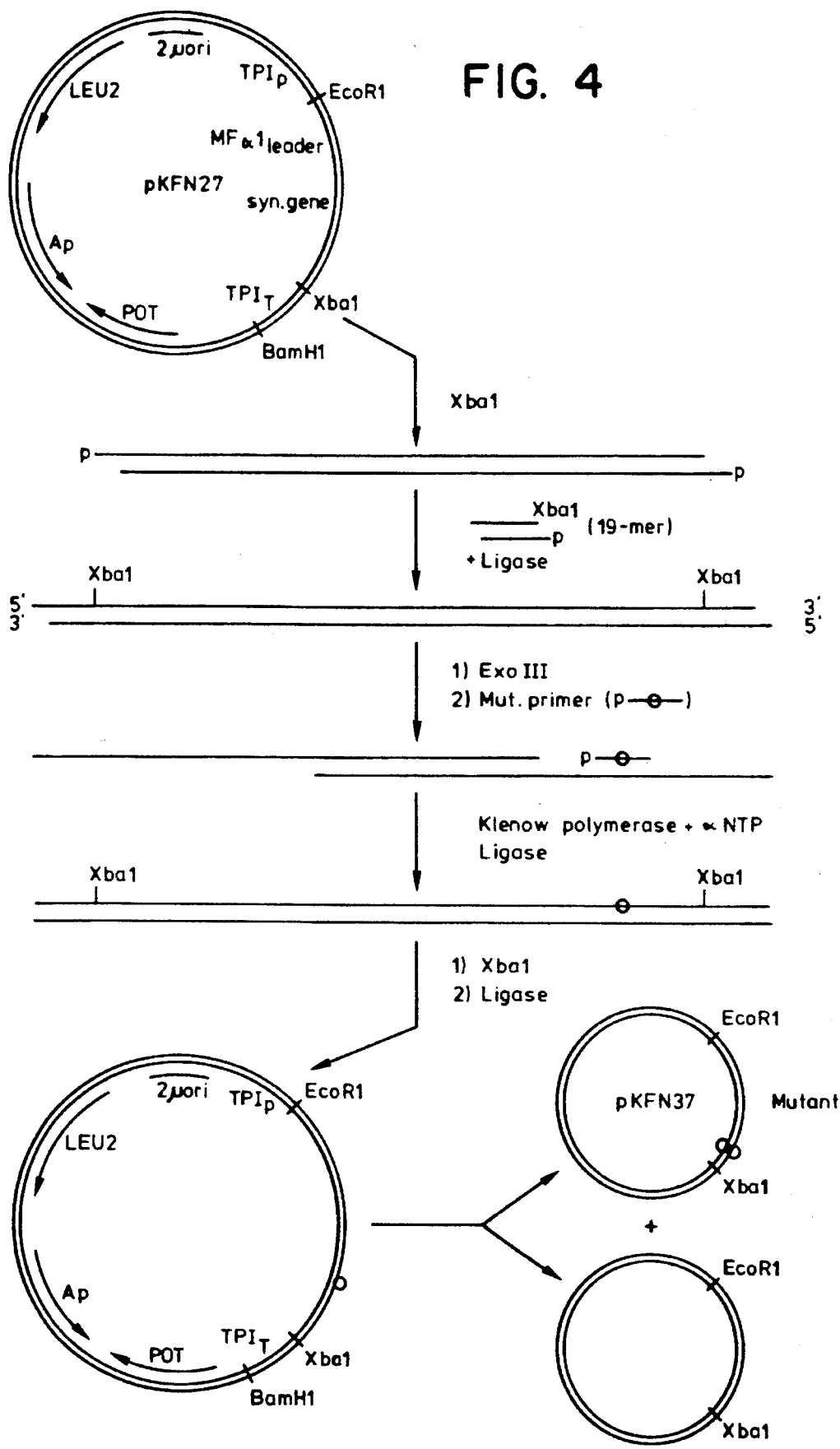
FIG. 4 shows the construction of a gene encoding B27Glu, B(1–29)-Ala-Ala-Lys-A(1–21) insulin.

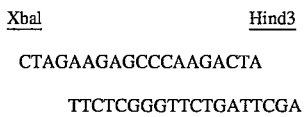

was ligated to each end of the linearized plasmid. The linker was 5'-phosphorylated at the Xba1 single stranded end but was left unphosphorylated at the Hind3 end, thereby avoiding polymerization of the linker during the ligation step and circularization of the DNA, see FIG. 4.

5'-mononucleotides were removed from the 3'-ends of the obtained linear double stranded DNA by means of ExoIII nuclease treatment. The ExoIII nuclease treatment was performed at 23° C. under conditions where about 250 nucleotides were removed from each 3'-end of the DNA (L. Guo and R. Wu (1983), Methods in Enzymology 100, 60–96).

A 5'-phosphorylated 25-mer mutagenesis primer d(GTTTCTTCTACGAACCTAAGGCTGC) was annealed to the mutation site. After filling in with Klenow polymerase in the presence of T4 ligase the double stranded DNA was digested with Xba1. Then heteroduplex circular DNA with the mutation in one strand was formed with T4 ligase.

The ligation mixture was transformed into *E. coli* (r⁻,m⁺) (MT172) selecting for ampicillin resistance.

Mutants were identified by colony hybridization with the 5'-32P-labelled 25-mer mutagenesis primer. After retransformation plasmid pKFN37 from one of the resulting colonies was shown to contain the desired mutation by DNA sequencing of a 0.5 kb Xba1-EcoR1 fragment (A. Maxam and W. Gilbert (1980) Methods in Enzymology 65, 499–560).

II. Transformation

*S. cerevisiae* strain MT663 (E2-7B×E11-3C a/α, Δ tpi/α tpi, pep 4-3/pep 4-3) was grown on YPGaL (1% Bacto yeast extract, 2% Bacto peptone, 2% galactose, 1% lactate) to an $OD_{600nm}$ of 0.6.

100 ml of culture was harvested by centrifugation, washed with 10 ml of water, recentrifuged and resuspended in 10 ml of 1.2M sorbitol, 25 mM Na$_2$EDTA pH=8.0, 6.7 mg/ml dithiotreitol. The suspension was incubated at 30° C. for 15 minutes, centrifuged and the cells resuspended in 10 ml of 1.2M sorbitol, 10 mM Na$_2$EDTA, 0.1M sodium citrate pH=5.8, 2 mg Novozym® 234. The suspension was incubated at 30° C. for 30 minutes, the cells collected by centrifugation, washed in 10 ml of 1.2M sorbitol and in 10 ml of CAS (1.2M sorbitol, 10 mM CaCl$_2$, 10 mM Tris (Tris=Tris(hydroxymethyl)-aminometan) pH=7.5) and resuspended in 2 ml of CAS. For transformation 0.1 ml of CAS-resuspended cells were mixed with approximately 1 μg of plasmid pKFN37 and left at room temperature for 15 minutes. 1 ml of 20% polyethylenglycol 4000, 10 mM CaCl$_2$, 10 mM Tris pH=7.5 was added and the mixture left for further 30 minutes at room temperature. The mixture was centrifuged and the pellet resuspended in 0.1 ml of SOS (1.2M sorbitol, 33% v/v YPGaL, 6.7 mM CaCl$_2$, 14 μg/ml leucine) and incubated at 30° C. for 2 hours. The suspension was then centrifuged and the pellet resuspended in 0.5 ml of 1.2M sorbitol. 6 ml of top agar (the SC medium of Sherman et al., (Methods in Yeast Generics, Cold Spring Harbor Laboratory, 1981) with leucine omitted and containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant KFN40 (=MT663/pKFN37) was chosen for further characterization.

III. Expression of B27Glu, B(1–29)-Ala-Ala-Lys-A(1–21) Insulin Precursor

Yeast strain KFN40 was grown on YPD medium (1% yeast extract, 2% peptone, (both from Difco laboratories), and 2% glucose). A 10 ml culture of the strain was shaken at 30° C. to an $OD_{600}$ of 26. After centrifugation the supernatant was analyzed by reversed phase HPLC and 13.5 mg/l precursor was found.

The analogue in the supernatant was concentrated on a cation exchange column at low pH followed by desorption with a suitable buffer solution. Crystallization was performed with an alcoholic citrate buffer.

IV. Transpeptidation 0.2 mole (47.1 g) Thr-OBu$^t$ HOAC was dissolved in DMF to give 100 ml solution, 50 ml 76.5% v/v DMF in water was added and 10 g of crude B27Glu, B(1–29)-Ala-Ala-Lys-A(1–21) human insulin was dissolved in the mixture, which was thermostated at 12° C. Then 1 g of trypsin in 25 ml 0.05M calcium acetate was added and after 24 h at 12° C. the mixture was added to 2 liter of acetone and the precipated peptides were isolated by centrifugation and dried in vacuo. The B27Glu, B30Thr-OBu$^t$ human insulin was purified on a preparative HPLC column with silica-C18 as column material.

V. Conversion into B27 Human Insulin

The B27Glu, B30Thr-OBu$^t$ human insulin was dissolved in 100 ml triflour acetic acid. After 2 hours at room temperature the solution was lyophilized. The lyophilized powder was dissolved in 400 ml 47.5 mM sodium citrate at pH 7. The peptides were precipitated at pH 5.5 after addition of 2.4 ml 1M ZnCl$_2$, isolated by centrifugation and dried in vacuo. The product was purified by anion exchange chromatography and desalted by gel filtration. Yield: 1.7 g of B27Glu human insulin.

EXAMPLE 3

Preparation of B9Asp Human Insulin

B9Asp human insulin was prepared by transpeptidation of B9Asp, B(1–29)-Ala-Ala-Lys-A(1–21) human insulin with Thr-OBu$^t$ and acidolysis of the obtained threonine ester with triflour acetic acid.

I. Construction of a Gene encoding B9Asp, B(1–29)-Ala-Ala-Lys-A(1–21) Human Insulin This gene was constructed in the same manner as described for the gene encoding B27Glu, B(1–29)-Ala-Ala-Lys-A(1–21) human insulin by site specific mutagenesis of pKFN27 directed by a 23-mer mutagenesis primer d(CT-TGTGCGGTGACCACTTGGTTG). Plasmid pKFN38 was shown to contain the desired mutation.

II. Transformation

Plasmid pKFN38 was transformed into *S. cerevisiae* strain MT663 by the same procedure as in example 2, II and a transformant KFN41 was isolated.

III. Expression of B9Asp, B(1–29)-Ala-Ala-Lys-A(1–21) Human Insulin

Yeast strain KFN41 was grown on YPD medium as described in example 2,III. 2.5 mg/l of the insulin analogue precursor was found in the supernatant.

IV. Transpeptidation 7.4 g of crude B9Asp, B(1–29)-Ala-Ala-Lys-A(1–21) human insulin was transpeptidated as described in example 2, IV to give B9Asp, B30Thr-OBu$^t$ human insulin.

V. Conversion

The B9Asp, B30Thr-OBu$^t$ human insulin was converted into B9Asp human insulin as described in example 2, V. Yield: 0.83 g B9Asp human insulin.

EXAMPLE 4

Preparation of B9Asp, B27Glu Human Insulin

B9Asp, B27Glu human insulin was prepared by transpeptidation of B9Asp, B27Glu B(1–21)-Ala-Ala-Lys-A(1–21) human insulin with Thr-OBu$^t$ and acidolysis of the obtained threonine ester with triflour acetic acid.

Figure 5:
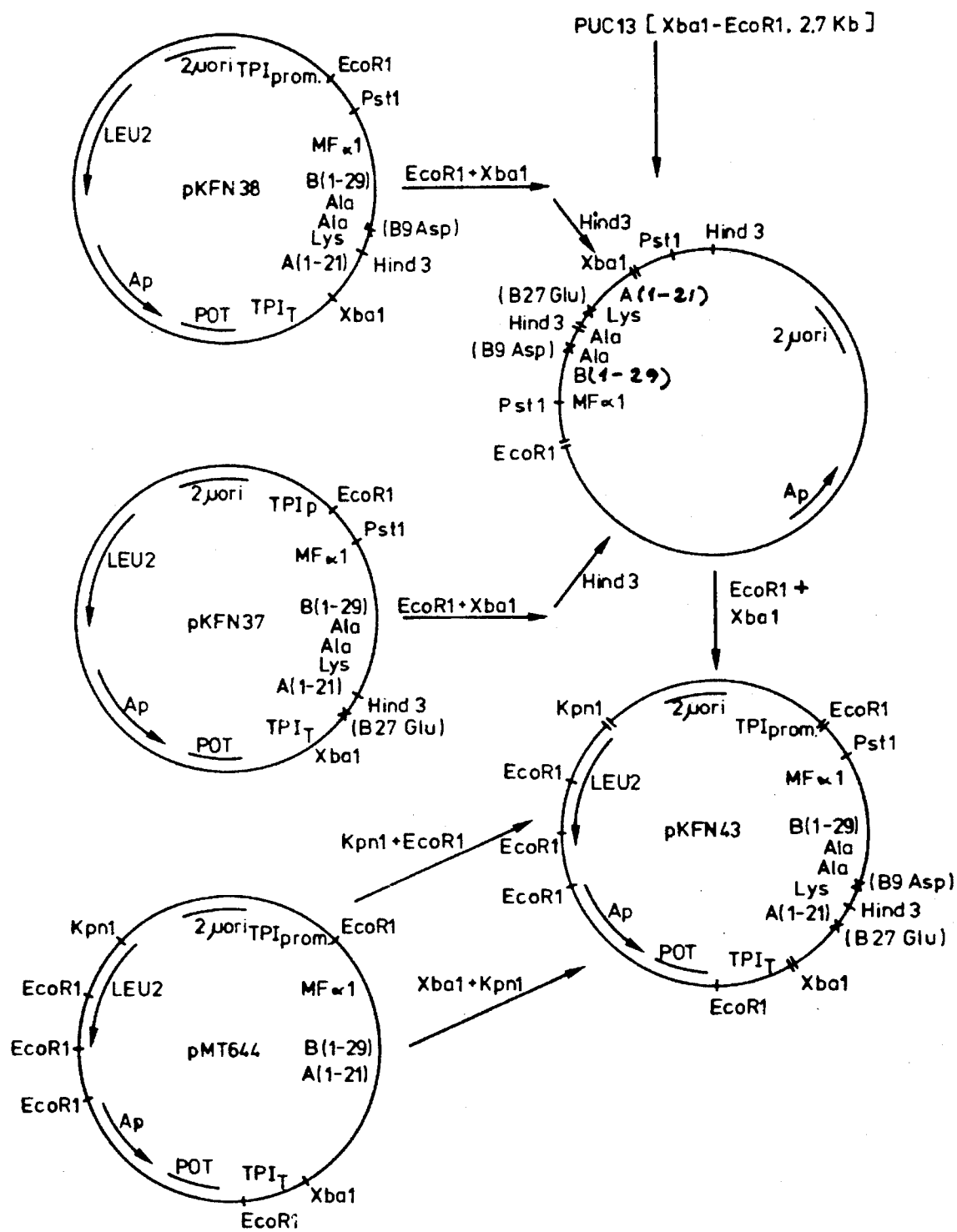
FIG. 5 shows the construction of plasmid pKFN43.

I. Construction of a Gene Encoding B9Asp,B27Glu,B(1–29)-Ala-Ala-Lys-A(1–21) Human Insulin A 367 bp EcoR1-Hind3 fragment from pKFN38 (see example 3) and a 140 bp Hind3-Xba1 fragment from pKFN37 (see example 2) were ligated to the large Xba1-EcoR1 fragment of plasmid pUC13 (this plasmid was constructed as described for pUC8 and pUC9 by Vieira et al. (1982), Gene 19, 259–268). The ligation mixture was transformed into *E. coli* (MT 172) selecting for ampicillin resistance. Plasmids were prepared from a number of transformants and analyzed by digestion with Pst1 and with Hind3. The 0.5 kb Xba1-EcoR1 fragment from one plasmid, which showed the correct restriction enzyme patterns, was ligated to a 7.8 kb Xba1-Kpn1 fragment and a 4.3 kb Kpn1-EcoR1 fragment both from pMT644 (described in Danish patent application No.1293/84). The ligation mixture was transformed into *E. coli* (MT172) selecting for ampicillin resistance. Plasmid pKFN43 from one of the resulting colonies was shown to contain the gene for the desired insulin derivative precursor by DNA sequencing of a 0.5 kb Xba1-EcoR1 fragment. The construction of pKFN43 is illustrated in FIG. 5.

II. Transformation

Plasmid pKFN38 was transformed into *S. cerevisiae* strain MT663 by the same procedure as in example 2, II and a transformant KFN44 was isolated.

III. Expression of B9Asp,B27Glu, B(1–29)-Ala-Ala-Lys-A(1–21) Human Insulin

Yeast strain KFN44 was grown on YPD medium as described in example 2, III. 7.3 mg/l of the insulin analogue precursor was found in the supernatant.

IV. Transpeptidation 12.7 g of crude B9Asp,B27Glu, B(1–29)-Ala-Ala-Lys-A(1–21) human insulin was transpeptidated as described in example 2, IV to give B9Asp,B27Glu,B30Thr-OBu$^t$ human insulin.

V. Conversion

The B9AsD,B27Glu,B30Thr-OBu$^t$ human insulin was converted into B9Asp,B27Glu,B30Thr human insulin and purified as described in example 2,V. Yield: 1.0 g B9Asp, B27Glu human insulin.

EXAMPLE 5

Preparation of A8His,B9Asp,B27Glu Human Insulin

A8His,B9ASp,B27Glu human insulin was prepared by transpeptidation of A8His,B9Asp,B27Glu, B(1–29)-Ala-Ala-Lys-A(1–21) human insulin with Thr-OBu$^t$ and acidolysis of the obtained threonine ester with triflour acetic acid as described in example 2.

I. Construction of a Gene Encoding A8His,B9Asp,B27Glu, B(1–29)-Ala-Ala-Lys-A(1–21) Human Insulin This gene was constructed by oligonucleotide directed mutagenesis using a gapped duplex procedure (Y. Morinaga, T. Franceschini, S. Inouye, and M. Inouye (1984), Biotechnology 2, 636–639). The pUC13 derived plasmid encoding the MFα1 leader sequence and the B9Asp,B27Glu human insulin precursor (FIG. 5) was cut with HpaI and XbaI. The large fragment was mixed with the plasmid linearized with NdeI. After heat denaturation and cooling the mixture contains gapped duplexes with a single stranded "window" in the region corresponding to the insulin precursor gene (HpaI-XbaI). The 37-mer mutagenic mismatch primer d(GAACAATGCTGTCACTCCATCTGCTC-CTTGTACCAAT) was hybridized to the gapped duplex followed by filling in with Klenow polymerase and ligation. The mixture was used to transform *E. coli* (MT172) selecting for ampicillin resistance. Mutants were identified by colony hybridization with an 18-mer 5'-$^{32}$P-labelled probe d(AATGCTGTCACTCCATCT). After retransformation a plasmid from one of the resulting colonies was shown to contain the desired mutation by DNA sequencing of a 0.5 kb XbaI-EcoRI fragment. This plasmid was used for construction of the yeast plasmid pKFN 102 as described in example 4 for the construction of pKFN43.

II. Transformation

Plasmid pKFN102 was transformed into *S. cerevisiae* strain MT663 by the same procedure as in example 2, II and a transformant KFN109 was isolated.

III. Expression of A8His,B9Asp,B27Glu, B(1–29)-Ala-Ala-Lys-A(1–21) Human Insulin Yeast strain KFN109 was grown on YPD medium as described in example 2, III. 21.5 mg/l of the insulin analogue precursor was found in the supernatant.

IV-V. Transpeptidation and Conversion 22.0 g crude A8His,B9Asp,B27Glu, B(1–29)-Ala-Ala-Lys-A(1–21) human insulin was transpeptidated, converted and purified as described in example 2, IV-V. Yield: 4.0 g A8HisB9AspB27Glu human insulin.

B12Ile human insulin was prepared by transpeptidation of B12Ile, B(1–29)-Ala-Ala-Lys-A(1–21) human insulin with Thr-OBu$^t$ and acidolysis of the obtained threonine ester with triflour acetic acid as described in example 2.

I. Construction of a Gene Encoding B12Ile, B(1–29)-Ala-Ala-Lys-A(1–21) Human Insulin A 0.5 kb EcoR1-Xba1 fragment of pMT598 (the construction of plasmid pMT598 is described in EP patent application No. 0163529A) encoding MFα1 leader (minus Glu-Ala-Glu-Ala)-B(1–29)-Ala-Ala-Lys-A(1–21) was inserted into M13 mp10 RF phage cut with XbaI-EcoRI and the corresponding single strand DNA was purified from the M13 mp10 recombinant phage. The single strand template DNA was hybridized to a mutagenic 27 mer primer NOR-92 d(GTAGAGAGCTTCGATCAGGTGTGAGCC) and a M13 universal sequencing primer d(TCCCAGTCACGACGT). The primers were extended by dNTPs and Klenow polymerase and ligated by T4 DNA ligase. The mutagenic primer KFN92 was chosen so as to destroy a BstN1 site (unique in the Xba1-EcoR1 fragment). Therefore, to select against unmutated EcoR1-Xba1 fragment, the mixture was cut with BstN1 and subsequently with EcoR1 and Xba1, and ligated to EcoR1 and Xba1 cut pUC13 vector. From one of the transformants obtained, a plasmid, pMT760, lacking the BstN1 site in the insulin coding sequence was chosen. The desired mutated sequence was verified by Maxam-Gilbert DNA sequencing. Plasmid pMT760 contains a 0.5 kb EcoR1-Xba1 sequence corresponding to the same fragment from pMT598 (see above) apart from a mutation at B12 (Val - Ile). This mutated sequence was then moved onto a yeast expression plasmid by ligation of the 0.5 kb EcoR1-Xba1 fragment of pMT760 to a 7.8 kb Xba1-Kpn1 and a 4.3 kb Kpn1-EcoR1 fragment from pMT644 to give pMTA.

II-V. Transformation, Expression, Transpeptidation, Conversion

Plasmid pMTA was transformed into yeast strain MT663 as described in example 2, II and the transformant strain MTA was grown as described in example 2, III. 10.4 mg/l of the insulin analogue precursor was found in the supernatant. 10 g of the crude analogue precursor was transpeptidated, converted and purified as described in example 2, IV-V. Yield: 1.3 g of B12Ile human insulin.

EXAMPLE 7

Preparation of B12Tyr Human Insulin

B12Tyr, human insulin can be prepared by transpeptidation of B12Tyr, B(1–29)-Ala-Ala-Lys-A(1–21) human insulin with Thr-OBu$^t$ and acidolysis of the obtained threonine ester with triflour acetic acid as described in example 2.

I. Construction of a Gene Encoding B12Tyr, B(1–29)-Ala-Ala-Lys-A(1–21) Human Insulin The gene was constructed by a method analogue to the method for the preparation of the gene encoding B12Ile, B(1–29)-Ala-Ala-Lys-A(1–21) human insulin with the only exception that primer KFN93 d(GTAGAGAGCTTCGTA-CAGGTGTGAGCC) was used instead of KFN92.

II-IV. Transformation, Expression, Transpeptidation, Conversion

Steps II–III were performed as described in example 2. 1.7 mg/l of the insulin analogue precursor was found in the supernatant. The crude analogue precursor can be transpeptidated, converted and purified as described in example 2, VI-V to give B12Tyr human insulin.

EXAMPLE 8

Preparation of B10Asp Human Insulin

B10 Asp human insulin was prepared by transpeptidation of B10Asp, B(1–29)-Ala-Ala-Lys-A(1–21) human insulin with Thr OBu$^t$ and acidolysis of the obtained threonine ester with triflour acetic acid as described in example 2.

I. Construction of a Gene Encoding B10Asp, B(1–29)-Ala-Ala-Lys-A(1–21) Human Insulin The gene was constructed by a method analogue to the method for the preparation of the gene encoding B12Ile, (B(1–29)-Ala-Ala-Lys-A(1–21) human insulin with the only exception that primer KFN94 d(AGCTTCCACCAGATCT-GAGCCGCACAG) was used instead of KFN 92.

II-V. Transformation, Expression, Transpeptidation, Conversion

Steps II–III were performed as described in example 2. 36 mg/l of the insulin analogue precursor was found in the supernatant. The crude analogue precursor was transpeptidated, converted and purified as described in example 2, IV-V. Yield: 7.6 g of B10Asp human insulin.

EXAMPLE 9

Preparation of B28Asp Human Insulin

B28Asp human insulin was prepared by transpeptidation of B28Asp, B(1–29)-Ala-Ala-Lys-A(1–21) human insulin with Thr-OMe and hydrolysis of the obtained threonine ester at a pH of about 8 to 12.

I. Construction of a Gene Encoding B28Asp, B(1–29)-Ala-Ala-Lys-A(1–21) Human Insulin A 0.5 kb EcoR1-Xba1 fragment of pMT 462 (the construction of plasmid pMT 462 is described in Danish patent application No. 1257/86) encoding the MFα1 leader (minus Glu-Ala-Glu-Ala)-B-C-A, i.e. the human proinsulin gene preceded by the modified MFα1 leader, was inserted into M13 mp10 RF phage cut with Xba1-EcoR1 and the corresponding single strand DNA was purified from the M13 mp10 recombinant phage. The single strand template DNA was hybridized to a mutagenic 41 mer primer NOR205 d(TTCCACAATGCCCTTAGCGGCCT-TGTCTGTGTAGAAGAAGC) and a M13 universal sequencing primer d(TCCCAGTCACGACGT). The primers were extended by dNTPs and Klenow polymerase and ligated by T4 DNA ligase.

After phenol extraction, ethanol precipation and resuspension, the DNA was cut with restriction enzymes Apa 1, Xba1 and EcoR1. After another phenol extraction, ethonal precipitation and resuspension, the DNA was ligated to EcoR1-Xba1 cut pUC13. The ligation mixture was transformed into an E. coli (r$^-$m$^+$) strain and plasmids were prepared from a number of transformants. Plasmid preparations were cut with EcoR1 and Xba1 and those preparations showing bands at both 0.5 and 0.6 kb were retransformed into E. coli. From the retransformation a transformant harbouring only pU13 with a 0.5 insert was selected.

From one of the transformants obtained a plasmid pMT881 with the desired mutation at B28 (Pro→Asp) was chosen. The mutated sequence was verified by Maxam-Gilbert DNA sequencing. The mutated sequence was then moved onto a yeast expression plasmid by ligation of a 0.5 kb EcoR1-Xba1 fragment of pMT881 to a 7.8 kb Xba1-Kpn1 and a 4.3 kb Kpn1-EcoR1 fragment from pMT644 to give pMTA1.

II. Transformation

Plasmid pMTA1 was transformed into S. cerevisiae strain MT663 by the same procedure as in example 2, II and a transformant MTA1 was isolated.

III. Expression of B28Asp, B(1–29)-Ala-Ala-Lys-A(1–21) Human Insulin

Yeast strain MTA1 was grown on YPD medium as described in example 2, III. 7.2 mg/l of the insulin analogue precursor was found in the supernatant.

IV. Transpeptidation

The crude B28Asp,B(1–29)-Ala-Ala-Lys-A(1–21) was transpeptidated as described in example 2, IV by substituting Thr-OBu$^t$ with Thre-OMe to give B28Asp,B30Thr-OMe human insulin.

V. Conversion

The B28Asp,B30Thr-OMe human insulin was dispersed in water to 1% (w/v) and was dissolved by addition of 1N sodium hydroxide to a pH value of 10.0. The pH value was kept constant at 10.0 for 24 hours at 25° C. The B28Asp human insulin formed was precipitated by addition of sodium chloride to about 8% (w/v), sodium acetate trihydrate to about 1.4% (w/v), and zinc acetate dihydrate to about 0.01% (w/v) followed by addition of 1N hydrochoric acid to pH 5.5. The precipitate was isolated by centrifugation and purified by anion exchange chromotography and desalted by gel filtration. Yield: 0.2 g B28Asp human insulin.

EXAMPLE 10

Preparation of A21Asp,B9Asp,B27Glu Human Insulin

A21Asp,B9Asp,B27Glu human insulin was prepared from B9Asp,B27Glu human insulin by selective deamidation (hydrolysis of a 5% solution for 14 days at 37° C., pH 2.5). The deamidated product was isolated by anion exchange chromatography.

EXAMPLE 11

Preparation of B27Glu,A21Asp Human Insulin

B27Glu,A21Asp human insulin was prepared by transpeptidation of B27Glu,A21Asp, B(1–29)-Ala-Ala-Lys-A (1–21) with ThrOBu$^t$ and acidolysis of the obtained threonine ester with triflour acetic acid as described in example 2.

B27GluA21AspB(1–29)-Ala-Ala-Lys-A(1–21) was prepared from B27Glu,B(1–29)-Ala-Ala-Lys-A(1–21) (see example 2) by deamidation as described in example 10.

Characterization of Human Insulin Analogue of the Present Invention

Determination of molecular weights (Gutfreund H. Biochemical Journal 42 (544) 1948)

Method: Knauer Membran Osmometer Type: 1.00
Membran: Schleicher and Schell Type: R52
Solvent: 0.05M NaCl pH 7.5 Temp.: 21° C.

Results: All types of insulin were measured at a concentration of 4 mg/ml

TABLE 1

| Type of insulin | Molecular weight k Dalton |
| --- | --- |
| Human 2Zn insulin | 36 ± 2 |
| Human Zn free insulin | 29 ± 1 |
| Zn free B27Glu human insulin | 22 ± 1 |
| — — B12Ile human insulin | 17 ± 1 |
| — — B27Glu, A21Asp human insulin | 8 ± 1 |
| — — B9Asp, B27Glu human insulin | 6 ± 1 |
| — — B9Asp human insulin | 6 ± 1 |
| — — B9Asp, B27Glu, A21Asp human insulin | 6 ± 1 |
| — — B9Asp, B27Glu, A8His human insulin | 9 ± 3 |
| — — B10Asp human insulin | 12 ± 1 |
| — — B28Asp human insulin | 9 ± 2 |

It appears from the above table 1 that the human insulin analogues have a markedly reduced molecular weight compared with human insulin meaning that the self-associating into dimers, tetramers and hexamers is less pronounced or in several cases even lacking.

TABLE 2

| | Half life and Biological potency | |
| --- | --- | --- |
| Human insulin analogue | $T_{1/2}$* (% of human insulin) | Biological potency** % of human insulin (95% conf. interval) |
| B27Glu human insulin | 78 | 101 (83–123) |
| B9Asp, B27Glu human insulin | 54 | 110 (90–139) |
| B12Ile human insulin | 78 | 91 (80–103) |
| B27Glu, A21Asp human insulin | 56 | 64 (58–71) |
| B9Asp human insulin | 52 | 80 (72–90) |
| A21Asp, B9Asp, B27Glu human insulin | 56 | 75 (66–85) |
| A8His, B9Asp, B27Glu human insulin | 68 | 116 (101–135) |
| B10Asp human insulin | 64 | 104 (92–18) |
| B28Asp human insulin |  | 104 (95–114) |

*Time to 50% disappearance from injection site (subcut.) in pigs. Method according to Binder 1969 (Acta Pharmacol. Toxiccl (suppl 2) 27:1–87)
**Mouse Blood Glucose Assay according to European Pharmacopocia.

It appears from the above table 2 that the time to 50% disappearance of the insulin analogues from the injection site is substantially reduced when compared with human insulin.

The biological potency of the insulin analogues is comparable with human insulin or only slightly reduced.

We claim:

1. Rapid acting human insulin analogues, characterized in that they have the formula I

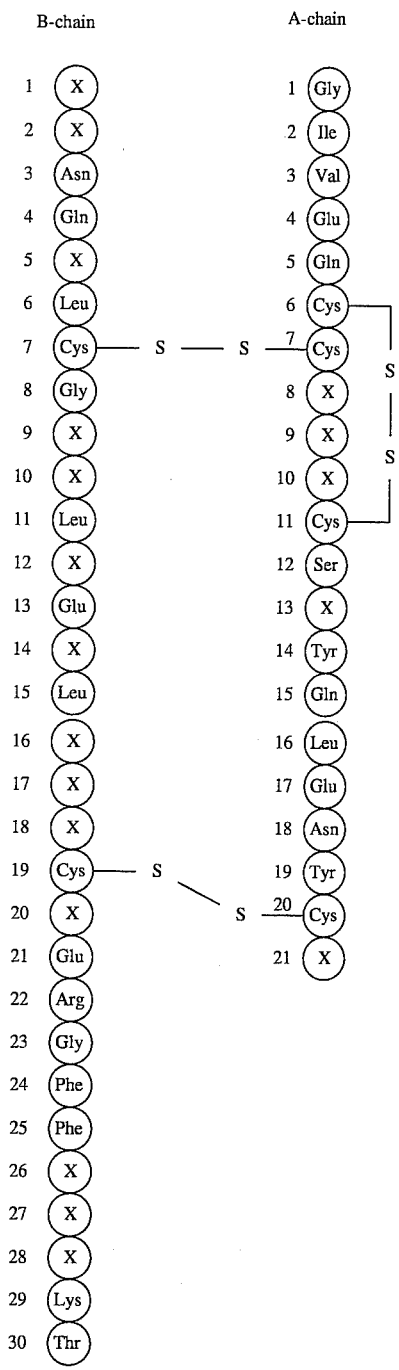

wherein except as indicated hereinafter the X's are the amino acid residues of human insulin and at least one but not more than 4× is different from the amino acid residue of human insulin at the respective position in the insulin molecule the net function of which substitution(s) is to impart to the molecule the same charges or a greater negative charge at neutral pH than that of human insulin, with the proviso that when X in position B(5) is Ala, or when X in position B(9) is Leu; or when X in position B(10) is Asn or Leu; or when X in position B(12) is Asn; or when X in position B(26) is Ala, then at least one of the remaining X's is different from the amino acid residues of human insulin at the respective position in the insulin molecule and with the further proviso that at least one substitution is at an X in the B-chain but X in position B(10) is not Asp.

2. Insulin analogues according to claim 1, wherein the amino acid residue substitutions are more hydrophilic than the amino acid residue of human insulin at the respective position in the insulin molecule.

3. Human insulin analogues according to claim 1, wherein the amino acid substitutions are selected from the group consisting of Glu, Ser, Thr, His, and Ile.

4. Human insulin analogues according to claim 1, wherein the amino acid residue substitution is Glu.

5. Human insulin analogues according to claim 1, wherein at least one X in position B(9), B(10), B(12), B(26), B(27), or B(28) is different from the amino acid residue at the corresponding site in the molecule of human insulin.

6. Injectable solutions with insulin activity, characterized in that they contain a human insulin analogue according to claim 1 or a pharmaceutically acceptable salt thereof in aqueous solution preferably at neutral pH.

7. Human insulin analogues according to claim 1 with at least one B-chain amino acid residue substitution therein from the following list:

| |
|---|
| B(9): Asp, Glu, His, Gln or Asn; |
| B(10): Arg, Glu, Asn, Gln, Ser, Thr, Ile; |
| B(12): His, Ile, or Tyr; |
| B(16): Asp, Glu, Gln, Asn, Ser, Thr or His; |
| B(17): Ser, Thr, Asn, Gln, Glu, Asp, or His; |
| B(20): Ser, Thr, Asn, Gln, Asp, Glu or His; |
| B(26): Asp, Glu, Asn, Gln, Ser, Thr or His; |
| B(27): Asp, Glu or His; |
| B(28): Asp, Glu or His. |

8. Human insulin analogues according to claim 7, wherein one or more of said substitutions at position B(9), B(10), B(16), B(27) and B(28) are combined with 1 to 3 substituents from the following list:

| |
|---|
| A(8): His, Gly, Gln, Glu, Ser, Asn, Pro or Asp; |
| A(13): His, Glu, Asp, Thr, Ser, Asn or Gln; |
| A(21): Asp or Glu; |
| B(1): Glu, Asp, Thr or Ser; |
| B(2): Arg, His Ala, Glu, Asp, Thr, Pro, Gly, Gln, Ser or Asn. |

9. Human insulin analogues according to claim 7, wherein one or more of said substitutions at position B(9), B(17), B(27), or B(28) are combined with one substitution in B(14) selected from the group consisting of Glu, Asp, Asn, Gln, Ser, Thr and Gly.

10. Human insulin analogues according to claim 7, wherein one of said substitutions is combined with one substitution in B(18) selected from the group consisting of Ser, Thr, Asn, Glu and His.

11. Human insulin analogues according to claim 1 wherein from 2–4 residues are different from the amino acid residue of human insulin.

12. Rapid acting human insulin analogues, characterized in that they have the Formula I

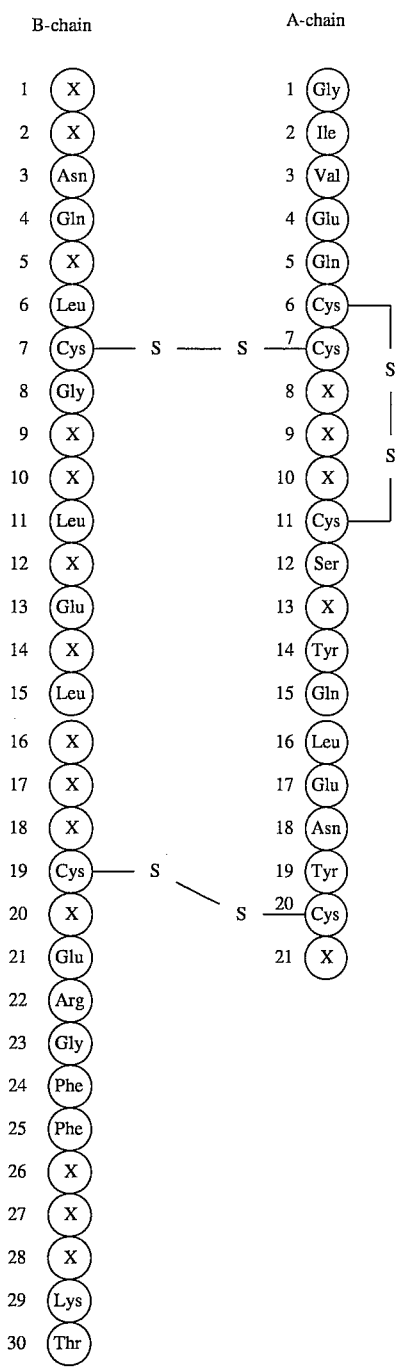

wherein except as indicated hereinafter the X's are the aamino acid residues of human insulin at least 1 but not more than 4 being different from the amino acid residue of human insulin at the respective position in the insulin molecule, with the proviso when X in position B(9) is Leu; or when X in position B(10) is Asn then at least one of the remaining X's are different from the amino acid residues of human insulin at the respective position in the insulin molecule and with the further proviso that at least one X in the B-chain is different, the net function of which substitution(s) being to impart to the molecule the same charge or a greater negative charge at neutral pH than that of human insulin, said substitution(s) being selected from the following:

| Position | Amino acid residue substitutions |
|---|---|
| A8 | His, Gly, Gln, Glu, Ser, Asn, Asp, Pro |
| A9 | Gly, Asp, Glu, Thr, His, Gln, Asn, Ala, Pro |
| A10 | Le, Pro, Val, His, Ala, Glu, Asp, Thr, Gln, Asn |
| A13 | Pro, Val, Arg, His, Ala, Glu, Asp, Thr, Gly, Gln, Asn, Asp, Ser, Thr |
| A21 | Asp, Glu, Ser, Thr |
| B1 | Glu, Asp, Thr, Ser, Gly |
| B2 | Arg, His, Ala, Glu, Asp, Thr, Pro, Gly, Gln, Ser, Asn |
| B5 | Glu, Asp, Thr, Ser, Gln, Asn |
| B9 | Asp, Pro, Glu, Ile, Leu, Val, His, Thr, Gln, Asn, Met, Tyr, Trp, Phe |
| B10 | Arg, Glu, Asn, Gln, Ser, Thr |
| B12 | Ile, Tyr |
| B14 | Glu, Asp, Asn, Gln, Ser, Thr, Gly |
| B16 | Asp, Glu, Gln, Asn, Ser, Thr, His, Arg |
| B17 | Ser, Thr, Asn, Gln, Glu, Asp, His |
| B18 | Ser, Thr, Asn, Gln, His |
| B20 | Gln, Ser, Asn, Asp, Glu, Arg, Thr |
| B26 | Asp, Glu, Ser, Thr |
| B27 | Asp, Glu |
| B28 | Asp, Glu. |

13. Human insulin analogues selected from the group consisting of B(27) Glu human insulin, B(12) Ile human insulin, B(12) Tyr human insulin, A(21) Asp B(27) Gtu human insulin, B(9) Asp human insulin, A(21) Asp B(9) Asp B(27) Glu human insulin, B(9) Asp B(27) Glu human insulin, and B(28) Asp human insulin, said analogues being characterized by rapid acting insulin activity.

14. A human insulin analogue according to claim 13, wherein the human insulin analogue is B(28) Asp human insulin.

* * * * *